(12) United States Patent
Heider et al.

(10) Patent No.: US 6,582,849 B1
(45) Date of Patent: Jun. 24, 2003

(54) STABLE $(CF_3)_2N^-$ SALTS AND PROCESS FOR PREPARING THEM

(75) Inventors: Udo Heider, Riedstadt (DE); Michael Schmidt, Weiterstadt (DE); Peter Sartori, Rheinberg (DE); Nikolai Ignatev, Duisburg (DE); Adrji Kucherna, Duisburg (DE)

(73) Assignee: Merck Patent Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 09/654,519

(22) Filed: Sep. 1, 2000

(30) Foreign Application Priority Data

Sep. 1, 1999 (DE) .......................................... 199 41 566

(51) Int. Cl.[7] .............................................. H01M 6/14
(52) U.S. Cl. ........................ 429/188; 252/62.2; 361/505
(58) Field of Search ................................ 429/188, 189, 429/307; 252/62.2; 361/505

(56) References Cited

U.S. PATENT DOCUMENTS 5,827,602 A    10/1998    Koch et al.

OTHER PUBLICATIONS

European Search Report dated Jan. 22, 2001 for EP00 118126.
Chemical Abstracts; 84: 150135w; Bis(trifluoromethyl)azanion, vol. 84, 1976, No month.
Novel Ammonium Hexafluoroarsenate Salts From Reaction of $(CF_3)_2NH$, $CF_3N(OCF_3)H$, $CF_3N[OCF(Cf_3)_2]H$, $CF_3NHF$ and $SF_5NHF$ with the Strong Acid $HF/AsF_5$; Journal of Fluorine Chemistry, 25 (1984) 387–394, No month.

R. Minkwitz et al.; Contribution to the Chemisty of Bis(Trifluoromethyl)amines: Preparation of Bis(Trifluoromethyl)Ammonium Hexafluorometalates $(CF_3)_2NH_2+MF_6-$ (M= As, Sb). Crystal Structure of $(CF_3)_2NH_2+Asf_6-$ and Gas–Phase Structures of $(CF_3)_2nX$ (X=H, Cl); Inorg. Chem. 1994, 33, 1817–1821, No month.

R. Minkwitz et al.; Preparation and Spectroscopic Characterization of $Cf_3$–Substituted Amides, Phosphides, an Arsenides, $M(CF_3)_2-$ (M–N, P, As)); Inorg. Chem. 1989, 28, 1627–1630, No month.

Chemical Abstracts, vol. 84, 1976, p. 538; 84: 121781y Generation and certain reactions of bis(tri =fluoromethyl)azanion, No month.

Emeleus et al. ("Bis(trifluoromethyl) amino sulfur compounds", J. Inorg. Nucl. Chem. (1966), 28(9), 1823–7, Caplus abstract only).*

* cited by examiner

*Primary Examiner*—Patrick Ryan
*Assistant Examiner*—Susy Tsang-Foster
(74) *Attorney, Agent, or Firm*—Millen, White, Zelano & Branigan, P.C.

(57) ABSTRACT

The invention relates to stable $(CF_3)_2N^-$ salts, to a process for preparing them and to their use as precursor for organic compounds.

21 Claims, No Drawings

STABLE $(CF_3)_2N^-$ SALTS AND PROCESS FOR PREPARING THEM

The invention relates to stable $(CF_3)_2N^-$ salts, to a process for preparing them and to their use as precursor for organic compounds.

Lithium ion batteries are amongst the most promising systems for mobile applications. The areas of application extend from high-quality electronic appliances (e.g. mobile phones, camcorders) to batteries for electrically driven motor vehicles.

These batteries consist of a cathode, an anode, a separator and a non-aqueous electrolyte. The cathodes used are typically $Li(MnMe_z)_2O_4$, $Li(CoMe_z)O_2$, $Li(CoNi_xMe_z)O_2$ or other lithium intercalation and insertion compounds. Anodes can consist of lithium metal, carbon materials, graphite, graphitic carbon materials or other lithium intercalation and insertion compounds or alloy compounds. The electrolytes used are solutions containing lithium salts, such as $LiPF_6$, $LiBF_4$, $LiClO_4$, $LiAsF_6$, $LiCF_3SO_3$, $LiN(CF_3SO_2)_2$ or $LiC(CF_3SO_2)_3$ and mixtures thereof, in aprotic solvents.

During the search for novel salts for use in batteries, the class of bis(trifluoromethyl)amines was identified as suitable.

One of the first salts described in the literature from the class of bis(trifluoromethyl)amines is caesium bis(trifluoromethyl)amide. This salt can be prepared by introducing perfluoro(2-azapropane) into a suspension of caesium fluoride and dry acetonitrile. Minkwitz (Inorg. Chem., 28 (1989), 1627–1630) isolates $Cs^+{}^-N(CF_3)_2$, but neither $(C_6H_5)_4As^+$ $(CF_3)_2N^-$ nor $(C_2H_5)_4N^+$ $(CF_3)_2N^-$.

European application 99101982 describes a new method for preparing the $(CF_3)_2N^-$ anion with an inorganic cation. The salts are stable only in solution and thus have to be used directly.

SUMMARY OF THE INVENTION

The object of the present invention is therefore to provide stable $(CF_3)_2N^-$ salts and a process for preparing them.

The object according to the invention is achieved by compounds of the general formula

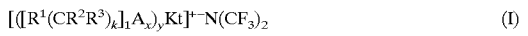

where
- Kt is N, P, As, Sb, S or Se,
- A is N, P, P(O), O, S, S(O), $SO_2$, As, As(O), Sb or Sb(O),
- $R^1$, $R^2$ and $R^3$ are identical or different and are each H, halogen, substituted and/or unsubstituted alkyl $C_nH_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl $C_mH_{2m-1}$, mono- or polysubstituted and/or unsubstituted phenyl, substituted and/or unsubstituted heteroaryl,
- Kt can be included in a cyclic or heterocyclic ring, where the ring may number from 4–8 atoms. A heterocyclic ring may include at least one atom of O, N, P As, Sb, S, Se or combinations thereof. Exemplary rings including Kt are disclosed in U.S. Pat. No. 5,827,602, which is hereby incorporated by reference,
- the groups bonded to Kt may be identical or different, where
  - n is 1–18
  - m is 3–7
  - k is 0 or 1–6
  - l is 1 or 2 in the case where x=1 and 1 in the case where x=0
  - x is 0 or 1
  - y is 1–4.

The compounds can be used as reagents for introducing $N(CF_3)_2$ groups into organic substances. For instance, it is possible to prepare fluorinated solvents for secondary and primary batteries.

Surprisingly, a further possible application for these salts was found. Owing to their structure, the novel salts are of interest as precursors for the preparation of liquid-crystal compounds.

It has been found that the simple preparation of the complex compounds can be conducted under mild conditions. The salts are isolated in high yields.

Surprisingly, it has been found that the novel salts are stable. They can be isolated and stored at room temperature.

A general example of the invention is explained in greater detail below.

Compounds of the general formula

where $D^+$ is selected from the group consisting of the metals, preferably alkali metals, are prepared by the process described in European patent application No. 99101982. Preferred alkali metals are Rb, Na, K, and Cs and other metals are Ag, Cu and Ag. A particularly preferred metal is Rb. Further suitable $N(CF_3)_2$-group providers are compounds of the general formula

where G is selected from the group consisting of fluorinated sulfonamides and fluorinated acylamides.

A solution of a compound of the general formula (II) or (IV) in a suitable polar organic solvent selected from the group consisting of acetonitrile, diethoxyethane and dimethylformamide is initially charged. A salt of the general formula

where
- Kt=N, P, As, Sb, S or Se,
- A=N, P, P(O), O, S, S(O), $SO_2$, As, As(O), Sb or Sb(O),
- $R^1$, $R^2$ and $R^3$ are identical or different and are each H, halogen, substituted and/or unsubstituted alkyl $C_nH_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl $C_mH_{2m-1}$, mono- or polysubstituted and/or unsubstituted phenyl, substituted and/or unsubstituted heteroaryl,
- Kt can be included in a cyclic or heterocyclic ring, where the ring may number from 4–8 atoms. A heterocyclic ring may include at least one atom of O, N, P As, Sb, S, Se or combinations thereof. Exemplary rings including Kt are disclosed in U.S. Pat. No. 5,827,602,
- the groups bonded to Kt may be identical or different, where
  - n=1–18
  - m=3–7
  - k=0 or 1–6
  - l=1 or 2 in the case where x=1 and 1 in the case where x=0 x=0 or 1 y=1–4 and $^-E = F^-$, $Cl^-$, $Br^-$, $I^-$, $BF_4^-$, $ClO_4^-$, $AsF_6^-$, $SbF_6^-$ or $PF_6^-$
is added in equimolar amounts, at temperatures between −40° C. and 80° C., preferably at room temperature.

Any volatile by-products which may form are removed by applying a reduced pressure. However, the by-products formed are usually salts which are insoluble in these solvents and which are filtered off.

The solvent is removed under reduced pressure. The reaction products can be obtained in yields of more than 80%. Most salts are stable at room temperature and do not decompose on melting.

The novel compounds can be used in electrolytes comprising conventional conductive salts. Examples of suitable electrolytes are those comprising conductive salts selected from the group consisting of $LiPF_6$, $LiBF_4$, $LiClO_4$, $LiAsF_6$, $LiCF_3SO_3$, $LiN(CF_3SO_2)_2$ and $LiC(CF_3SO_2)_3$ and mixtures thereof. The electrolytes may further comprise organic isocyanates (DE 199 44 603) to reduce the water content. Likewise, the electrolytes may comprise organic alkali metal salts (DE 199 10 968) as additives. Suitable alkali metal salts are alkali metal borates of the general formula $$Li^+B^-(OR^1)_m(OR^2)_p$$

where m and p are 0, 1, 2, 3 or 4 with m+p=4 and $R^1$ and $R^2$ are identical or different, if desired are joined directly to one another by a single or double bond, and are, in each case individually or together, an aromatic or aliphatic carboxylic, dicarboxylic or sulfonic acid radical, or are, in each case individually or together, an aromatic ring selected from the group consisting of phenyl, naphthyl, anthracenyl and phenanthrenyl, which may be unsubstituted or monosubstituted to tetrasubstituted by A or Hal, or are, in each case individually or together, a heterocyclic aromatic ring selected from the group consisting of pyridyl, pyrazyl and bipyridyl, which may be unsubstituted or monosubstituted to trisubstituted by A or Hal, or are, in each case individually or together, an aromatic hydroxy acid selected from the group consisting of aromatic hydroxycarboxylic acids and aromatic hydroxysulfonic acids, which may be unsubstituted or monosubstituted to tetrasubstituted by A or Hal, and Hal is F, Cl or Br and A is alkyl having from 1 to 6 carbon atoms, which may be monohalogenated to trihalogenated. Likewise suitable are alkali metal alkoxides of the general formula.

$$Li^+OR^-$$

where R is an aromatic or aliphatic carboxylic, dicarboxylic or sulfonic acid radical, or is an aromatic ring selected from the group consisting of phenyl, naphthyl, anthracenyl and phenanthrenyl, which may be unsubstituted or monosubstituted to tetrasubstituted by A or Hal, or is a heterocyclic aromatic ring selected from the group consisting of pyridyl, pyrazyl and bipyridyl, which may be unsubstituted or monosubstituted to trisubstituted by A or Hal, or is an aromatic hydroxy acid selected from the group consisting of aromatic hydroxycarboxylic acids and aromatic hydroxysulfonic acids, which may be unsubstituted or monosubstituted to tetrasubstituted by A or Hal, and Hal is F, Cl or Br, and A is alkyl having from 1 to 6 carbon atoms, which may be monohalogenated to trihalogenated.

Lithium complex salts of the formula

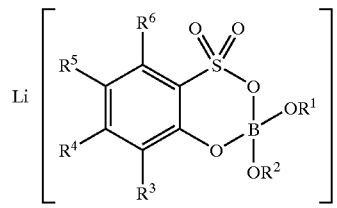

where $R^1$ and $R^2$ are identical or different, if desired are joined directly to one another by a single or double bond, and are, in each case individually or together, an aromatic ring selected from the group consisting of phenyl, naphthyl, anthracenyl and phenanthrenyl, which may be unsubstituted or monosubstituted to hexasubstituted by alkyl ($C_1$ to $C_6$), alkoxy groups ($C_1$ to $C_6$) or halogen (F, Cl, Br), or are, in each case individually or together, an aromatic heterocyclic ring selected from the group consisting of pyridyl, pyrazyl and pyrimidyl, which may be unsubstituted or monosubstituted to tetrasubstituted by alkyl ($C_1$ to $C_6$), alkoxy groups ($C_1$ to $C_6$) or halogen (F, Cl, Br), or are, in each case individually or together, an aromatic ring selected from the group consisting of hydroxybenzenecarboxyl, hydroxynaphthalenecarboxyl, hydroxybenzenesulfonyl and hydroxynaphthalenesulfonyl, which may be unsubstituted or monosubstituted to tetrasubstituted by alkyl ($C_1$ to $C_6$), alkoxy groups ($C_1$ to $C_6$) or halogen (F, Cl, Br), $R^3$–$R^6$ can, in each case individually or in pairs, if desired joined to one another directly by a single or double bond, have the following meanings:

1. alkyl ($C_1$ to $C_6$), alkyloxy ($C_1$ to $C_6$) or halogen (F, Cl, Br)
2. an aromatic ring selected from the groups phenyl, naphthyl, anthracenyl and phenanthrenyl, which may be unsubstituted or monosubstituted to hexasubstituted by alkyl ($C_1$ to $C_6$), alkoxy groups ($C_1$ to $C_6$) or halogen (F, Cl, Br), pyridyl, pyrazyl and pyrimidyl, which may be unsubstituted or monosubstituted to tetrasubstituted by alkyl ($C_1$ to $C_6$), alkoxy groups ($C_1$ to $C_6$) or halogen (F, Cl, Br), which are prepared by the following method (DE 199 32 317)

a) 3-, 4-, 5-, 6-substituted phenol is admixed in a suitable solvent with chlorosulfonic acid, b) the intermediate from a) is reacted with chlorotrimethylsilane, and the product is filtered and subjected to fractional distillation, c) the intermediate from b) is reacted with lithium tetramethoxyborate(1-) in a suitable solvent and the end product is isolated therefrom, can also be present in the electrolyte.

However, use can also be made of electrolytes comprising compounds of the general formula (DE 199 53 638)

$$X-(CYZ)_m-SO_2N(CR^1R^2R^3)_2$$

where
- X is H, F, Cl, $C_nF_{2n+1}$, $C_nF_{2n-1}$ or $(SO_2)_kN(CR^1R^2R^3)_2$,
- Y is H, F or Cl
- Z is H, F or Cl
- $R^1$, $R^2$ and $R^3$ are H and/or alkyl, fluoroalkyl or cycloalkyl
- m is 0–9 and, if X=H, m≠0
- n is 1–9
- k is 0 if m=0 and k=1 if m=1–9, prepared by reacting partially fluorinated or perfluorinated alkylsulfonyl fluorides with dimethyl-amine in organic solvents, and also complex salts of the general formula (DE 199 51 804)

$$M^{x+}[EZ]_{x/y}{}^{y-}$$

where:
- x, y are 1, 2, 3, 4, 5 or 6
- $M^{x+}$ is a metal ion
- E is a Lewis acid selected from the group consisting of $BR^1R^2R^3$, $AlR^1R^2R^3$, $PR^1R^2R^3R^4R^5$, $AsR^1R^2R^3R^4R^5$ and $VR^1R^2R^3R^4R^5$,
- $R^1$ to $R^5$ are identical or different, if desired are joined directly to one another by a single or double bond, and may be, in each case individually or together,
  - a halogen (F, Cl, Br),
  - an alkyl or alkoxy radical ($C_1$ to $C_8$) which may be partially or fully substituted by F, Cl, Br,
  - an aromatic ring, if desired bonded via oxygen, selected from the group consisting of phenyl, naphthyl, anthracenyl and phenanthrenyl, which may be unsubstituted or monosubstituted to hexasubstituted by alkyl ($C_1$ to $C_8$) or F, Cl, Br,
  - an aromatic heterocyclic ring, if desired bonded via oxygen, selected from the group consisting of pyridyl, pyrazyl and pyrimidyl, which may be unsubstituted or monosubstituted to tetrasubstituted by alkyl ($C_1$ to $C_8$) or F, Cl, Br, and
- Z is $OR^6$, $NR^6R^7$, $CR^6R^7R^8$, $OSO_2R^6$, $N(SO_2R^6)$ $(SO_2R^7)$, $C(SO_2R^6)$ $(SO_2R^7)$ $(SO_2R^8)$ or $OCOR^6$, where
  - $R^6$ to $R^8$ are identical or different, if desired are joined directly to one another by a single or double bond, and are, in each case individually or together,
  - a hydrogen or as defined for $R^1$ to $R^5$, prepared by reacting a corresponding boron or phosphorus Lewis acid-solvent adduct with a lithium or tetraalkylammonium imide, methanide or triflate.

Borate salts (DE 199 59 722) of the general formula

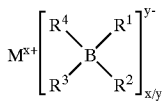

where:
- M is a metal ion or tetraalkylammonium ion,
- x, y are 1, 2, 3, 4, 5 or 6,
- $R^1$ to $R^4$ are identical or different alkoxy or carboxyl radicals ($C_1$–$C_8$) which may be joined directly to one another by a single or double bond may also be present. These borate salts are prepared by reacting lithium tetraalkoxyborate or a 1:1 mixture of lithium alkoxide and a boric ester in an aprotic solvent with a suitable hydroxyl or carboxyl compound in the ratio 2:1 or 4:1.

The novel compounds can also be used in electrolytes comprising lithium fluoroalkylphosphates of the general formula (I)

$$Li^+[PF_x(C_yF_{2y+1-z}H_z)_{6-x}]^- \qquad (I)$$

where
- $1 \leq x \leq 5$
- $3 \leq y \leq 8$
- $0 \leq z \leq 2y+1$ and the ligands $(C_yF_{2y+1-z}H_z)$ can be identical or different, with the exception of compounds of the general formula (I')

$$Li^+[PF_a(CH^bF_c(CF_3)_d)_e]^- \qquad (I')$$

in which
- a is an integer from 2 to 5, b=0 or 1, c=0 or 1, d=2 and
- e is an integer from 1 to 4, with the provisos that b and c are not simultaneously 0 and the sum of a+e is 6 and the ligands $(CH_bF_c(CF_3)_d)$ can be identical or different (DE 100 089 55). The process for preparing lithium fluoroalkylphosphates of the general formula (I) is characterized in that at least one compound of the general formula $$H_mP(C_nH_{2n+1})_{3-m} \qquad (III),$$

$$OP(C_nH_{2n+1})_3 \qquad (IV),$$

$$Cl_mP(C''H_{2n+1})_{3-m} \qquad (V),$$

$$F_mP(C_nH_{2n+1})_{3-m} \qquad (VI),$$

$$Cl_oP(C''H_{2n+1})_{5-o} \qquad (VII),$$

$$F_oP(C_nH_{2n+1})_{5-o} \qquad (VIII),$$

where in each case
0<m<2, 3<n<8 and 0<o<4,
is fluorinated by electrolysis in hydrogen fluoride, the resulting mixture of fluorination products is fractionated by extraction, phase separation and/or distillation, and the resulting fluorinated alkylphosphorane is reacted with lithium fluoride in an aprotic solvent or solvent mixture in the absence of moisture, and the resulting salt of the general formula (I) is purified and isolated by customary methods.

The novel compounds can also be used in electrolytes comprising salts of the formula $$Li[P(OR^1)_a(OR^2)_b(OR^3)_c(OR^4)_dF_e]$$

where $0<a+b+c+d \leq 5$ and $a+b+c+d+e=6$, and $R^1$ to $R^4$ are each, independently of one another, alkyl, aryl or heteroaryl radicals, it being possible for at least two of $R^1$ to $R^4$ to be joined directly to one another by a single or double bond (DE 100 16801). These compounds are prepared by reacting phosphorus(V) compounds of the general formula $$P(OR^1)_a(OR^2)_b(OR^3)_c(OR^4)_dF_e$$

where $0<a+b+c+d \leq 5$ and $a+b+c+d+e=5$, and $R^1$ to $R^4$ are as defined above, with lithium fluoride in the presence of an organic solvent.

The novel compounds can be employed in electrolytes for electrochemical cells which comprise anode material consisting of coated metal cores selected from the group consisting of Sb, Bi, Cd, In, Pb, Ga and tin or alloys thereof (DE 100 16 024). The method for preparing said anode material is characterized in that a) a suspension or a sol of the metal core or alloy core is prepared in urotropine, b) the suspension is emulsified with $C_5$–$C_{12}$-hydrocarbons, c) the emulsion is precipitated onto the metal cores or alloy cores, and d) the metal hydroxides or oxyhydroxides are converted into the corresponding oxide by heat-treating the system.

The novel compounds can also be used in electrolytes for electrochemical cells comprising cathodes consisting of customary lithium intercalation and insertion compounds or else cathode materials consisting of lithium mixed oxide particles which are coated with one or more metal oxides (DE 199 22 522) by suspending the particles in an organic solvent, admixing the suspension with a solution of a hydrolysable metal compound and a hydrolysis solution and then filtering off, drying and, if desired, calcining the coated particles. They can also consist of lithium mixed oxide particles which are coated with one or more polymers (DE 199 46 066) and are obtained by a process in which the particles are suspended in a solvent and the coated particles are subsequently filtered off, dried and, if desired, calcined. Likewise, the novel compounds can be used in systems comprising cathodes which consist of lithium mixed oxide particles, which are singly or multiply coated with alkali metal compounds and metal oxides (DE 100 14 884). The method for preparing these materials is characterized in that the particles are suspended in an organic solvent, an alkali metal salt compound suspended in an organic solvent is added, metal oxides dissolved in an organic solvent are added, the suspension is admixed with a hydrolysis solution, and the coated particles are then filtered off, dried and calcined.

The reaction products of the general formula (I) are also used as $N(CF_3)_2$ group provider in various reagents. For instance, they can be used as precursor for liquid crystals.

Equimolar amounts of a compound selected from the group consisting of alkyl haloacetates, preferably ethyl bromoacetate, are added to a compound of formula (I) prepared in accordance with the invention which is dissolved in a suitable solvent. The mixture is refluxed for 1 to 4 hours, preferably for 2 hours. Water is added, and the organic phase is extracted using suitable organic solvents. The extract is dried and subsequently the solvent is removed by distillation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 199 41 566.8, filed Sep. 1, 1999 is hereby incorporated by reference.

EXAMPLES

Example 1

A solution of 4.63 g (19.5 mmol) of $Rb^{+-}N(CF_3)_2$ (prepared from 2.04 g (19.5 mmol) of RbF and 5.56 g (19.5 mmol) of $CF_3SO_2N(CF_3)_2$ in 20 cm³ of dry acetonitrile) is added to a solution of 6.40 g (19.4 mmol) of $(C_4H_9)_4N^+BF_4^-$ in 5 cm³ of dry acetonitrile at room temperature with stirring. Precipitated $RbBF_4$ is filtered off and washed with dry acetonitrile. After removal of the solvent under reduced pressure, 7.5 g of a white powder are isolated.

The $(C_4H_9)_4N^{+-}N(CF_3)_2$ yield is 98%.

Analysis:

|   | Found: | Calculated: |
| --- | --- | --- |
| C | 54.67 | 54.80 |
| H | 9.56 | 9.20 |
| F | 28.70 | 28.90 |
| N | 7.15 | 7.10 |

$^{19}$F NMR ($CCl_3F$): –38.32 s (solvent: $CH_3CN$), –37.66 s (solvent: $CD_2Cl_2$); melting point: 123–125° C.

Example 2

A solution of 0.568 g (2.39 mmol) of $Rb^{+-}N(CF_3)_2$ (prepared from 0.25 g (2.39 mmol) of RbF and 0.69 g (2.39 mmol) of $CF_3SO_2N(CF_3)_2$ in 2 cm³ of dry acetonitrile) is added to a solution of 0.66 g (2.37 mmol) of $(C_4H_9)_4N^+Cl^-$ in 1 cm³ of dry acetonitrile at room temperature. Precipitated RbCl is filtered off and washed with dry acetonitrile. After removal of the solvent by distillation under reduced pressure, 0.77 g of a white powder is isolated. The $(C_4H_9)_4N^{+-}N(CF_3)_2$ yield is 82.2%.

The $^{19}$F NMR spectrum is identical to that obtained in Example 1.

Example 3

A solution of 0.62 g (2.61 mmol) of $Rb^{+-}N(CF_3)_2$ (prepared from 0.273 g (2.61 mmol) of RbF and 0.75 g (2.63 mmol) of $CF_3SO_2N(CF_3)_2$ in 2 cm³ of dry acetonitrile) is added to a solution of 0.883 g (2.60 mmol) of $(C_4H_9)_4P^+Br^-$ in 1 cm³ of dry acetonitrile at room temperature. Precipitated RbBr is filtered off and washed with dry acetonitrile. After removal of the solvent by distillation under reduced pressure, 0.97 g of a white powder is isolated. The $(C_4H_9)_4P^{+-}N(CF_3)_2$ yield is 90.7%.

$^{19}$F NMR ($CCl_3F$): –36.49 s (solvent: $CH_3CN$); melting point: 85–86° C.

Example 4

A solution of 0.017 g (0.18 mmol) of $(CH_3)_4N^+F^-$ in 0.5 cm³ of dry dichloromethane is admixed with 0.052 g (0.18 mmol) of $CF_3SO_2N(CF_3)_2$ at –40° C. The reaction solution is warmed to room temperature, diluted with the same amount of dry acetonitrile and analysed by $^{19}$F NMR spectroscopy. The signal observed belongs to the salt $(CH_3)_4N^{+-}N(CF_3)_2$. After removal of the solvent by distillation in a dry argon atmosphere, 0.037 g of a white, highly hygroscopic material is isolated. The yield is 90.2%.

$^{19}$F NMR ($CCl_3F$): –40.8 s; melting point: 120–125° C.

Example 5

A solution of 0.837 g (2.12 mmol) of $(C_4H_9)_4N^{+-}N(CF_3)_2$ in 2 cm³ of dry dichloromethane is admixed with 0.271 g (1.62 mmol) of $BrCH_2COOC_2H_5$. The mixture is refluxed for 2 hours. Water is added and the organic phase is extracted three times with 10 cm³ of dichloromethane each time. The extract is dried over $MgSO_4$ and the solvent is removed by distillation. The resulting product, $(CF_3)_2NCH_2COOC_2H_5$, is identified by GC. The yield is 93.3%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula

   (I)

where
Kt=P, Sb, or Se,
A=N, P, P(O), O, S, S(O), $SO_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4.

2. A reagent for introducing $N(CF_3)_2$ groups into organic compounds, comprising the compound according to claim 1.

3. A compound according to claim 1, wherein $K_t$=P.

4. A process for preparing a compound of the formula

   (I)

where
Kt=N, P, As, Sb, S or Se,
A=N, P, P(O), O, S, S(O), $SO_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4;

wherein an alkali metal salt of the formula

   (II)

where $D^+$ is an alkali metal, is reacted in a polar organic solvent with a salt of the formula

   (III)

where
Kt=N, P, As, Sb, S or Se,
A=N, P, P(O), O, S, S(O), $SO_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4, and
$^-$E is $F^-$, $Cl^-$, $Br^-$, $I^-$, $BF_4^-$, $ClO_4^-$, $AsF_6^-$, $SbF_6^-$, or $PF_6^-$.

5. The process according to claim 4, wherein in the reaction is conducted in polar organic solvent of an acetonitrile, a diethoxyethane or a dimethylformamide.

6. The process according to claim 4, wherein the reaction is conducted at temperatures between –40° C. and 80° C.

7. The process according to claim 4 wherein a compound of the formula

   (IV)

wherein G is a fluorinated sulfonamide or fluorinated acylamide, is reacted in a polar organic solvent with a compound of the formula (III) wherein $^-$E=$F^-$.

8. The process according to claim 7, wherein the reaction is conducted at temperatures between –40° C. and 80° C.

9. The process according to claim 6, wherein in that the reaction is conducted in polar organic solvent of an acetonitrile, diethoxyethane or dimethylformamide.

10. The process according to claim 4, wherein the alkali metal is lithium, sodium or potassium.

11. An electrolyte comprising:
a compound of the formula

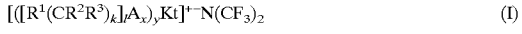   (I)

where
Kt=N, P, As, Sb, or Se,
A=N, P, P(O), O, S, S(O), $SO_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl, Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4; and
an alkali metal oxide of formula:

$$Li^+OR^-$$

where R
is an aromatic or aliphatic carboxylic, dicarboxylic or sulfonic acid radical, or is phenyl, naphthyl, anthracenyl or phenanthrenyl, which is optionally monosubstituted to tetrasubstituted by A or Hal, or
is a pyridyl, pyrazyl or bipyridyl, which is optionally monosubstituted to trisubstituted by A or Hal, or
is an aromatic hydroxycarboxylic acid or aromatic hydroxysulfonic acid, which is optionally monosubstituted to tetrasubstituted by A or Hal, and
Hal is F, Cl or Br, and
A is alkyl having from 1 to 6 carbon atoms, which is optionally monohalogenated to trihalogenated.

12. An electrolyte comprising:
a compound of the formula $$[([R^1(CR^2R^3)_k]_lA_x)_yKt]^+{}^-N(CF_3)_2 \quad (I)$$

where
Kt=N, P, As, Sb, or Se,
A=N, P, P(O), O, S, S(O), SO$_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4; and
a lithium complex salt of formula:

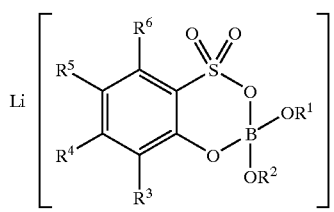

where
$R^1$ and $R^2$ are identical or different, optionally joined directly to one another by a single or double bond, and are, in each case individually or together, a phenyl, naphthyl, anthracenyl or phenanthrenyl, which is optionally monosubstituted to hexasubstituted by alkyl, alkoxy or halogen,
or are, in each case individually or together, a pyridyl, pyrazyl or pyrimidyl, which is optionally monosubstituted to tetrasubstituted by alkyl, alkoxy or halogen,
or are, in each case individually or together, a hydroxybenzenecarboxyl, hydroxynaphthalenecarboxyl, hydroxybenzenesulfonyl or hydroxynaphthalenesulfonyl, which is optionally monosubstituted to tetrasubstituted by alkyl, alkoxy or halogen,
$R^3$–$R^6$ optionally, in each case individually or in pairs, optionally joined to one another directly by a single or double bond, have the following meanings:
alkyl, alkyloxy or halogen; or
a phenyl, naphthyl, anthracenyl or phenanthrenyl, which is optionally monosubstituted to hexasubstituted by alkyl, alkoxy groups or halogen; or
a pyridyl, pyrazyl or pyrimidyl, which is optionally monosubstituted to tetrasubstituted by alkyl, alkoxy or halogen.

13. An electrolyte comprising:
a compound of the formula $$[([R^1(CR^2R^3)_k]_lA_x)_yKt]^+{}^-N(CF_3)_2 \quad (I)$$

where
Kt=N, P, As, Sb, or Se,
A=N, P, P(O), O, S, S(O), SO$_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4; and
a compound of formula:

$$X-(CYZ)_m-SO_2N(CR^1R^2R^3)_2$$

where
X is H, F, Cl, $C_nF_{2n+1}$, $C_nF_{2n-1}$ or $(SO_2)_kN(CR^1R^2R^3)_2$,
Y is H, F or Cl
Z is H, F or Cl
$R^1$, $R^2$ and $R^3$ are H and/or alkyl, fluoroalkyl or cycloalkyl
m is 0–9 and, if X=H, m$^1$≠0
n is 1–9; and
k is 0 if m=0 and k=1 if m=1–9.

14. An electrolyte comprising:

a compound of the formula $$[([R^1(CR^2R^3)_k]_lA_x)_yKt]^+ \ ^-N(CF_3)_2 \quad (I)$$

where
Kt=N, P, As, Sb, or Se,
A=N, P, P(O), O, S, S(O), SO$_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4; and a compound of formula:

$$M^{x+}[EZ]_{x/y}{}^{y-}$$

where:
x, y are 1, 2, 3, 4, 5 or 6;
$M^{x+}$ is a metal ion;
E is a Lewis acid of the formula:
BR$^1$R$^2$R$^3$, AlR$^1$R$^2$R$^3$, PR$^1$R$^2$R$^3$R$^4$R$^5$, AsR$^1$R$^2$R$^3$R$^4$R$^5$ or VR$^1$R$^2$R$^3$R$^4$R$^5$, wherein
$R^1$–$R^5$ are identical or different, optionally joined directly to one another by a single or double bond, and optionally, in each case individually or together,
a halogen,
an alkyl or alkoxy radical optionally substituted by F, Cl, Br,
an aromatic ring, optionally bonded via oxygen, of phenyl, naphthyl, anthracenyl or phenanthrenyl, which is optionally monosubstituted to hexasubstituted by alkyl or F, Cl, Br;
an aromatic heterocyclic ring, optionally bonded via oxygen, of pyridyl, pyrazyl or pyrimidyl, optionally monosubstituted to tetrasubstituted by alkyl or F, Cl, Br; and
Z is OR$^6$, NR$^6$R$^7$, CR$^6$R$^7$R$^8$, OSO$_2$R$^6$, N(SO$_2$R$^6$)(SO$_2$R$^7$), C(SO$_2$R$^6$)(SO$_2$R$^7$)(SO$_2$R$^8$) or OCOR$^6$, where
$R^6$ to $R^8$ are identical or different, optionally joined directly to one another by a single or double bond, and are, in each case individually or together,
a hydrogen or as defined for $R^1$ to $R^5$.

15. An electrolyte comprising:
a compound of the formula $$[([R^1(CR^2R^3)_k]_lA_x)_yKt]^+ \ ^-N(CF_3)_2 \quad (I)$$

where
Kt=N, P, As, Sb, or Se,
A=N, P, P(O), O, S, S(O), SO$_2$, As, As(O), Sb or Sb(O),
$R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4; and a compound of formula:

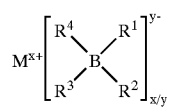

where:
M is a metal ion or tetraalkylammonium ion,
x, y are 1, 2, 3, 4, 5 or 6,
$R^1$ to $R^4$ are identical or different alkoxy or carboxyl radicals optionally joined directly to one another by a single or double bond.

16. An electrolyte comprising:
a compound of the formula $$[([R^1(CR^2R^3)_k]_lA_x)_yKt]^+ \ ^-N(CF_3)_2 \quad (I)$$

where
Kt=N, P, As, Sb, or Se,
A=N, P, P(O), O, S, S(O), SO$_2$, As, As(O), Sb or Sb(O),
$R^1$, $R^2$ and $R^3$ are each independently H, halogen, optionally substituted alkyl of formula $C_nH_{2n+}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4; and a lithium flororalkylphosphate of formula:

$$Li^+[PF_x(C_yF_{2y+1-z}H_z)_{6-x}]^- \quad (I)$$

where
$1 \leq x \leq 5$
$3 \leq y \leq 8$
$0 \leq z \leq 2y+1$ and the ligands ($C_yF_{2y+1-z}H_z$) are identical or different, with the exception of compounds of the general formula (I')

in which a is an integer from 2 to 5, b=0 or 1, c=0 or 1, d=2 and e is an integer from 1 to 4, with the provisos that b and c are not simultaneously 0 and the sum of a+e is 6 and the ligands ($CH_bF_c(CF_3)_d$) can be identical or different.

17. An electrolyte comprising:

a compound of the formula

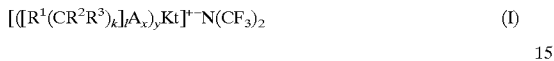

where

Kt=N, P, As, Sb, or Se,

A=N, P, P(O), O, S, S(O), $SO_2$, As, As(O), Sb or Sb(O), $R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl, Kt can be included in a cyclic or heterocyclic ring, the groups bonded to Kt may be identical or different, where n=1–18 m=3–7 k=0 or 1–6 l=1 or 2 in the case where x=1 and 1 in the case where x=0 x=0 or 1 y=1–4; and a salt of formula:

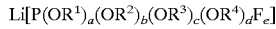

where $0<a+b+c+d \leq 5$ and a+b+c+d+e=6, and $R^1$ to $R^4$ are each, independently of one another, alkyl, aryl or heteroaryl radicals, optionally at least two of $R^1$ to $R^4$ are joined directly to one another by a single or double bond.

18. An electrolyte cell, comprising:

an electrolyte comprising a compound of the formula

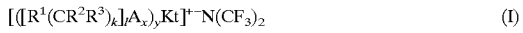

where

Kt=N, P, As, Sb, or Se,

A=N, P, P(O), O, S, S(O), $SO_2$, As, As(O), Sb or Sb(O), $R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl, Kt can be included in a cyclic or heterocyclic ring, the groups bonded to Kt may be identical or different, where n=1–18 m=3–7 k=0 or 1–6 l=1 or 2 in the case where x=1 and 1 in the case where x=0 x=0 or 1 y=1–4;

a cathode;

an anode; and a separator.

19. An electrolyte comprising a compound of the formula

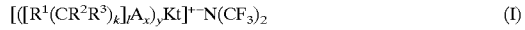

where

Kt =N, P, As, Sb, or Se,

A=N, P, P(O), O, S, S(O), SO, As, As(O), Sb or Sb(O), $R^1$, $R^2$ and $R^3$ are each independently H, halogen, optionally substituted alkyl of formula $C_nH_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula $C_mH_{2m-1}$, optionally mono- or polysubstituted phenyl, or optionally substituted heteroaryl, Kt can be included in a cyclic or heterocyclic ring, the groups bonded to Kt may be identical or different, where n=1–18 m=3–7 k=0 or 1–6 l=1 or 2 in the case where x=1 and 1 in the case where x=0 x=0 or 1 y=1–4;

and an alkali-metal borate of formula:

where m and p are 0, 1, 2, 3 or 4 with m+p=4 and $R^1$ and $R^2$ are identical or different, optionally joined directly to one another by a single or double bond, and are, in each case individually or together, an aromatic or aliphatic carboxylic, dicarboxylic or sulfonic acid radical, or are, in each case individually or together, phenyl, naphthyl, anthracenyl or phenanthrenyl, which is optionally monosubstituted to tetrasubstituted by A or Hal, or are, in each case individually or together, a pyridyl, pyrazyl or bipyridyl, which is optionally monosubstituted to trisubstituted by A or Hal, or are, in each case individually or together, an aromatic hydroxycarboxylic acid or an aromatic hydroxysulfonic acid, which is optionally monosubstituted to tetrasubstituted by A or Hal, and Hal is F, Cl or Br and A is alkyl having from 1 to 6 carbon atoms, which is optionally monohalogenated to trihalogenated.

20. A method of preparing a liquid-crystal compound by providing a reagent for introducing $N(CF_3)_2$ groups into organic compounds, comprising the compound of the formula

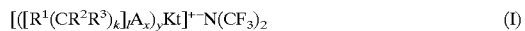

where
Kt=N, P, As, Sb, or Se,
A=N, P, P(O), O, S, S(O), SO$_2$, As, As(O), Sb or Sb(O),
R$^1$, R$^2$ and R$^3$ are each independently H, halogen, optionally substituted alkyl of formula C$_n$H$_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula C$_m$H$_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=1 and 1 in the case where x=0
x=0 or 1
y=1–4.

21. An electrochemical cell, comprising:
an electrolyte comprising a compound of the formula

 $[([R^1(CR^2R^3)_k]_lA_x)_yKt]^+{}^-N(CF_3)_2$ (I)

where
Kt=N, P, As, Sb, S or Se,
A=N, P, P(O), O, S, S(O), SO$_2$, As, As(O), Sb or Sb(O),
R$^1$, R$^2$ and R$^3$ are each independently H, halogen, optionally substituted alkyl of formula C$^n$H$_{2n+1}$, optionally substituted alkenyl having up to 18 carbon atoms and one or more double bonds, optionally substituted alkynyl having up to 18 carbon atoms and one or more triple bonds, optionally substituted cycloalkyl of formula C$_m$H$_{2m-1}$, optionally mono- or polysubstituted phenyl, or optionally substituted heteroaryl,
Kt can be included in a cyclic or heterocyclic ring,
the groups bonded to Kt may be identical or different,
where
n=1–18
m=3–7
k=0 or 1–6
l=1 or 2 in the case where x=0
x=0 or 1
y=1–4;
a cathode;
an anode; and
a separator.

* * * * *